(12) United States Patent
Huang et al.

(10) Patent No.: US 9,931,261 B2
(45) Date of Patent: Apr. 3, 2018

(54) MEDICAL PENDANT BOX BODY

(71) Applicant: MAQUET (SUZHOU) CO., LTD., Suzhou (CN)

(72) Inventors: Jiasheng Huang, Suzhou (CN); Wei Zhang, Suzhou (CN); Qunhua Li, Suzhou (CN); Ming Ji, Suzhou (CN)

(73) Assignee: MAQUET (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 15/335,784

(22) Filed: Oct. 27, 2016

(65) Prior Publication Data

US 2017/0049650 A1    Feb. 23, 2017

Related U.S. Application Data

(63) Continuation of application No. PCT/CN2014/083500, filed on Aug. 1, 2014.

(30) Foreign Application Priority Data

Apr. 30, 2014    (CN) .......................... 2014 1 0181214

(51) Int. Cl.
*E04F 19/00* (2006.01)
*A61G 12/00* (2006.01)
(Continued)

(52) U.S. Cl.
CPC ............ *A61G 12/002* (2013.01); *A61B 90/00* (2016.02); *A61B 90/08* (2016.02); *A61G 12/00* (2013.01);
(Continued)

(58) Field of Classification Search
CPC .... A61G 12/00; A61G 12/002; A61G 12/007; A61G 13/107; A61G 12/004; A61B 90/08; A61B 90/00
(Continued)

(56) References Cited

U.S. PATENT DOCUMENTS 4,429,355 A    1/1984  Garchinsky
4,475,322 A    10/1984 Russo et al.
(Continued)

FOREIGN PATENT DOCUMENTS

CN    201342036 Y    11/2009
CN    201358676 Y    12/2009
(Continued)

OTHER PUBLICATIONS

International Search Report dated Jan. 21, 2015, issued for corresponding application No. PCT/CN2014/083500, 3 pages.
(Continued)

*Primary Examiner* — Chi Q Nguyen

(57) ABSTRACT

A medical pendant box body is disclosed. The medical pendant box body has a first panel and a second panel, and a first post and a second post extending along a longitudinal direction of the medical pendant box body. The medical pendant box body also has an upper base plate and a lower base plate. The first panel is attached to the first post and the second panel is attached to the second post. The upper base plate is attached to an upper edge of each of the first and second panels, and the lower base plate is attached to a lower edge of each of the first and second panels. A snap-fit portion is disposed at a side edge portion of at least one of the first panel and the second panel.

19 Claims, 9 Drawing Sheets

(51) Int. Cl.
*A61B 90/00* (2016.01)
*A61G 13/10* (2006.01)

(52) U.S. Cl.
CPC .......... *A61G 12/004* (2013.01); *A61G 12/007* (2013.01); *A61G 13/107* (2013.01)

(58) Field of Classification Search
USPC ........................... 52/220.7, 27, 36.5, 36.6, 40
See application file for complete search history.

(56) References Cited

U.S. PATENT DOCUMENTS

| | | | |
|---|---|---|---|
| 5,644,876 A * | 7/1997 | Walker | A61G 13/107 211/26 |
| 5,805,075 A | 9/1998 | Carlson et al. | |
| 5,878,536 A | 3/1999 | Demmitt et al. | |
| D443,365 S * | 6/2001 | Walker | D24/232 |
| 6,256,935 B1 * | 7/2001 | Walker | A61G 13/107 52/220.1 |
| D452,573 S * | 12/2001 | Walker | D24/232 |
| 6,668,493 B1 * | 12/2003 | Walker | A61G 13/107 52/220.7 |
| 7,211,726 B2 * | 5/2007 | Bally | A61G 12/002 174/501 |
| 7,845,601 B1 | 12/2010 | Culpepper et al. | |
| 7,971,396 B1 * | 7/2011 | Culpepper | E04F 13/00 52/220.7 |
| 9,016,023 B2 * | 4/2015 | Timko | F21V 21/10 52/220.2 |
| 2004/0020675 A1 | 2/2004 | Bally et al. | |
| 2004/0231248 A1 | 11/2004 | Walker et al. | |
| 2010/0284731 A1 | 11/2010 | Bauer et al. | |
| 2017/0049650 A1 * | 2/2017 | Huang | A61G 12/00 |

FOREIGN PATENT DOCUMENTS

| | | |
|---|---|---|
| CN | 101940499 A | 1/2011 |
| CN | 201790896 U | 4/2011 |
| CN | 203483513 U | 3/2014 |
| CN | 103690245 A | 4/2014 |
| CN | 103908350 A | 7/2014 |
| CN | 203815592 U | 9/2014 |
| JP | H05-58594 A | 3/1993 |
| WO | 2009/096732 A2 | 8/2009 |

OTHER PUBLICATIONS

Singaporean Office Action (and accompanying Singaporean Search Report) dated Aug. 3, 2017, issued for corresponding Singaporean patent application No. 11201607077Y, 4 pages.

Japanese Office Action (with English translation) dated Sep. 4, 2017, issued for corresponding Japanese patent application No. 2016-572873, 7 pages.

Communication of supplementary European Search Report corresponding to EP application No. 14890543.3, 7 pages, dated Nov. 20, 2017.

* cited by examiner

MEDICAL PENDANT BOX BODY

CROSS REFERENCE TO RELATED APPLICATIONS

The present application is a continuation-in-part filed under 35 U.S.C. § 111(a), and claims the benefit under 35 U.S.C. § § 365(c) and 371 of PCT International Application No. PCT/CN2014/083500, filed Aug. 1, 2014, and which designates the United States of America, and Chinese Patent Application No. 201410181214.3, filed Apr. 30, 2014. The disclosures of these applications are herein incorporated by reference in their entirety.

TECHNICAL FIELD

The present disclosure relates to the technical field of medical equipment, and more particularly, for example, to a medical pendant box body.

BACKGROUND

A medical pendant system is a type of medical equipment used in modern hospital operating room, intensive care unit and the like. The main structure of a conventional medical pendant is a box body. The existing medical pendant box body is generally composed of panels and posts. The installation mode for the panels and posts of an existing medical pendant box body lies in that holes are formed in the two sides of the front of the panels, the panels are fixed to the posts using large number of installation screws in a fixed interval, and silica gel or rubber sealing strips are used to mask the screws after fixing with the screws.

Therefore, the existing medical pendant box body may have the following shortcomings. A large number of installation screws are involved, the installation is laborious and time-consuming, and the screws are exposed on the surface of the panels. Silica gel or rubber sealing strips are used to mask the screws after fixing with the screws if it is not desired for the screws to be exposed on the surface of the panels, but the use of silica gel or rubber sealing strips may not be suitable for cleaning and disinfection in hospitals.

SUMMARY OF THE DISCLOSURE

One of the purposes of the present disclosure is to overcome the above-mentioned disadvantages of the existing medical pendant box body. A medical pendant box body may be provided, which can be installed using a small amount of screws or even not using a screw to achieve the suitable connection of the panels and posts as well as the entire box body, without involving exposed screws on the surface of the panels, and without using the silica gel or rubber sealing strips to mask the screws. This may facilitate cleaning and disinfection, being capable of realizing the rapid disassembly and assembly of the medical pendant box body with in a relatively brief time.

The above purposes of the present disclosure may be achieved by a medical pendant box body, the medical pendant box body comprising at least two panels, at least two posts extending along the longitudinal direction of the medical pendant box body, an upper base plate and a lower base plate, the at least two panels being fixed to the at least two posts, respectively. The upper base plate and the lower base plate may be attached (e.g., fixed) to the upper edge and the lower edge of each panel of the at least two panels, respectively, a snap-fit portion being provided on each panel of the at least two panels at or in the vicinity of its at least one side edge, and a slot for receiving the corresponding snap-fit portion of the corresponding panel being provided on at least one side of each post of the at least two posts.

According to the above-mentioned technical solution, the medical pendant box body of the present invention can have the following technical features: it can be installed using a small amount of screws or for example not using a screw to achieve the suitable connection of the panels and posts as well as the entire box body, without exposed screws on the surface of the panels, without using the silica gel or rubber sealing strips to mask the screws, which facilitates the cleaning and disinfection, being capable of realizing the rapid disassembly and assembly of the medical pendant box body in a relatively short time.

In at least some exemplary embodiments, the upper base plate and the lower base plate may each comprise a through-hole at or the in the vicinity of its periphery for a base plate-fixing screw to pass through, and a base plate-fixing threaded hole for receiving the corresponding base plate-fixing screw may be provided at or in the vicinity of the upper edge and lower edge of each panel of the at least two panels.

In at least some exemplary embodiments, the medical pendant box body of the present disclosure can have the following technical features: the number of the screws used in the medical pendant box body of the present invention is (e.g., greatly) reduced as compared with the number of the screws used in a conventional medical pendant box body. Also, for example, there may be no exposed screws on the surface of the panels (e.g., without using the silica gel or rubber sealing strips to mask the screws), which may facilitate the cleaning and disinfection, being capable of realizing a relatively rapid disassembly and assembly of the medical pendant box body in a relatively short time.

In at least some exemplary embodiments, the at least two panels may include three panels, the at least two posts may be three posts, and the three panels may comprise two side panels with generally L-shaped cross section and one rear panel with generally I-shaped cross section.

In at least some exemplary embodiments, the medical pendant box body of the present disclosure can have the following technical features: a relatively simple medical pendant box body having relatively small space (e.g., of the box body) may be provided, which can be installed using a small amount of screws or alternatively not using a screw to achieve the suitable connection of the panels and posts as well as the (e.g., entire) box body, without exposed screws on the surface of the panels, being capable of realizing the rapid disassembly and assembly of the medical pendant box body.

In at least some exemplary embodiments, the cross section of the medical pendant box body may be generally square or trapezoidal.

In at least some exemplary embodiments, the medical pendant box body of the present invention can have the following technical features: a medical pendant box body having a desired cross section shape is provided, which can realize the simple and rapid disassembly and assembly of the medical pendant box body using less screws, meanwhile can more suitably accommodate the internal components of the box body.

In at least some exemplary embodiments, the at least two panels may include eight panels, the at least two posts may include four posts, the medical pendant box body may further comprise four auxiliary columns extending along the longitudinal direction of the medical pendant box body, the eight panels may comprise two side panels having generally L-shaped cross sections and six panels having generally I-shaped cross sections, in which the medical pendant box body may comprise two sub-box bodies, each sub-box body comprising one side panel having a generally L-shaped cross section, three panels having generally I-shaped cross sections, two posts, and two auxiliary columns.

In at least some exemplary embodiments, the medical pendant box body of the present disclosure can have the following technical features: a medical pendant box body having relatively large space of the box body and rational space distribution may be provided, which can be installed using a small amount of screws or alternatively not using a screw to achieve the suitable connection of the panels and posts as well as the entire box body, without exposed screws on the surface of the panels, being capable of realizing the rapid disassembly and assembly of the medical pendant box body.

In at least some exemplary embodiments, an overall (e.g., total) cross section of the medical pendant box body may be generally rectangular or trapezoidal, and the cross section of each sub-box body may be generally square or trapezoidal.

In at least some exemplary embodiments, the medical pendant box body of the present invention can have the following technical features: a medical pendant box body and its sub-box body having preferable cross section shape may be provided, which can realize the simple and rapid disassembly and assembly of the medical pendant box body using relatively few (e.g., less) screws, meanwhile can more appropriately accommodate the internal components of the box body.

In at least some exemplary embodiments, there may be an interval between the two sub-box bodies, which may form a hollow area from top to bottom.

In at least some exemplary embodiments, the medical pendant box body of the present disclosure can have the following technical features: the hollow area can be used as the cable management area of the medical pendant.

In at least some exemplary embodiments, the at least two panels may include eight panels, the at least two posts may be four posts, the medical pendant box body may further comprise four auxiliary columns extending along the longitudinal direction of the medical pendant box body, and the eight panels may comprise eight panels having generally I-shaped cross sections.

In at least some exemplary embodiments, the medical pendant box body of the present invention can have the following technical features: a medical pendant box body having relatively large space of the box body and rational space distribution may be provided, which can be installed using a small amount of screws or alternatively not using a screw to achieve the suitable connection of the panels and posts as well as the (e.g., entire) box body, without exposed screws on the surface of the panels, being capable of realizing the rapid disassembly and assembly of the medical pendant box body.

In at least some exemplary embodiments, the cross section of the medical pendant box body may be generally rectangular or trapezoidal.

In at least some exemplary embodiments, the medical pendant box body of the present disclosure can have the following technical features: a medical pendant box body having suitable cross section shapes being provided, which can realize the simple and rapid disassembly and assembly of the medical pendant box body using relatively less screws, and can more suitably accommodate the internal components of the box body.

In at least some exemplary embodiments, the auxiliary columns may be provided with panel-fixing thread grooves for receiving the panel-fixing screws so as to fix at least one panel to the auxiliary columns.

In at least some exemplary embodiments, the medical pendant box body of the present disclosure can have the following beneficial technical effect: the firmness of the medical pendant box body may be further reinforced through the additional fixation of the auxiliary columns and the panel-fixing screws.

In at least some exemplary embodiments, the medical pendant box body may also comprise a side cover plate for masking the panel-fixing screws.

In at least some exemplary embodiments, the medical pendant box body of the present disclosure can have the following technical features: in the case of setting the auxiliary columns and panel-fixing screws, the panel-fixing screws may be (e.g., effectively) masked, so that the screws may not be exposed on the surface of the panels, without using the silica gel or rubber sealing strips to mask the screws, which may facilitate the cleaning and disinfection.

In at least some exemplary embodiments, at least two spare thread grooves may be provided on the internal surface of each panel of the at least two panels.

In at least some exemplary embodiments, the medical pendant box body of the present disclosure can have the following technical features: the installation of the air port of the panel can be implemented without exposing screws, which may change the phenomenon that a large number of screws are exposed after installing the air port in the panels of the box body of the prior art, which may facilitate cleaning and disinfection in hospitals.

In at least some exemplary embodiments, the distances among the at least two spare thread grooves on each panel may be equal.

In at least some exemplary embodiments, the medical pendant box body of the present disclosure can have the following technical features: when electrical isolation is used among the panels, electrical separators can be made into a general part owing to the uniform interval among the spare thread grooves, so that the electrical separators of different panels can (e.g., entirely) be installed interchangeably, which may strengthen the versatility of the electrical separators.

In at least some exemplary embodiments, the medical pendant box body may also comprise a separator, the edge part of the separator pressing against the top surface of the periphery of the groove of the spare thread grooves via the head of the separator-fixing screw.

In at least some exemplary embodiments, the medical pendant box body of the present invention can have the following beneficial technical effect: the separator can be rapidly and simply installed on the panel without exposing the separator-fixing screw.

In at least some exemplary embodiments, the cross section of the separator may generally be in a shape which looks like the Chinese character "几 (ji)".

In at least some exemplary embodiments, the medical pendant box body of the present disclosure can have the following technical features: the electrical isolation can be achieved, and can also suitably accommodate the internal components of the box body.

In at least some exemplary embodiments, the medical pendant box body may also comprise auxiliary columns extending along the longitudinal direction of the medical pendant box body, the auxiliary columns being provided with panel-fixing thread grooves for receiving the panel-fixing screws so as to fix at least one panel to the auxiliary columns.

In at least some exemplary embodiments, the medical pendant box body of the present disclosure can have the following beneficial technical effect: the firmness of the medical pendant box body may be further reinforced through the additional fixation of the auxiliary columns and the panel-fixing screws.

DETAILED DESCRIPTION AND INDUSTRIAL APPLICABILITY

The present disclosure is further described in connection with drawings and particular embodiments as follows and elaborated in more detail in the following description. It is evident that the present disclosure can be implemented in many other ways which are different from those described herein; generalization and deduction can be made by a skilled in the art without departing from the connotation of the disclosure according to practical application, and therefore the protective scope of the present disclosure should not be limited by the specific content of exemplary embodiments herein.

Figure 1:
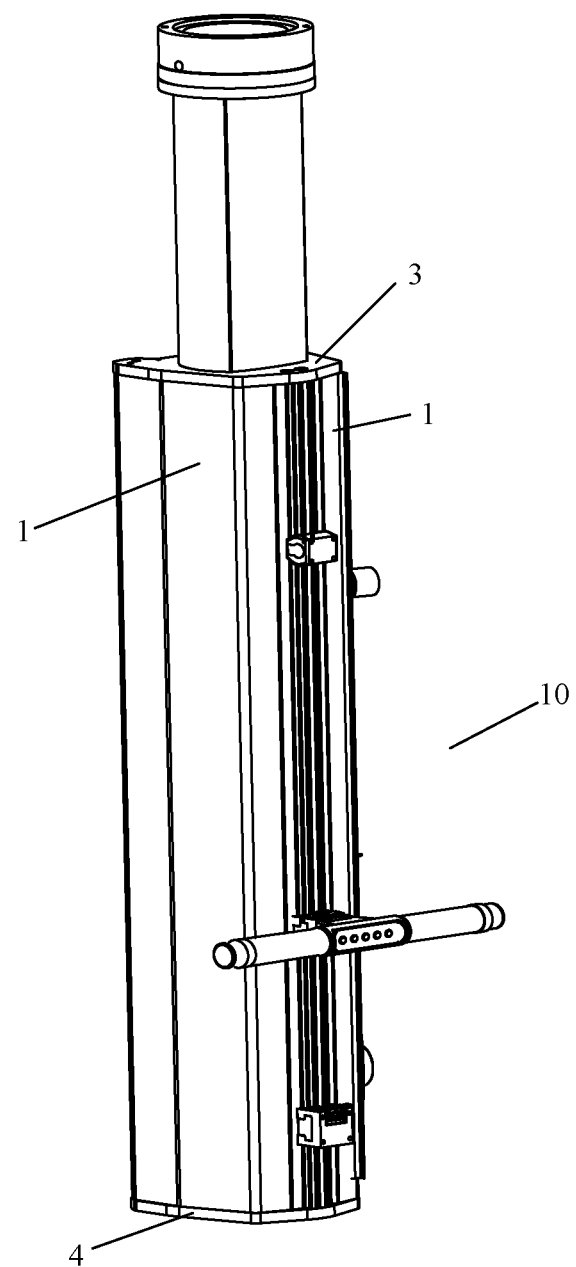
FIG. 1 is the three-dimensional view for the medical pendant box body of the first embodiment of the present disclosure.
Figure 2:
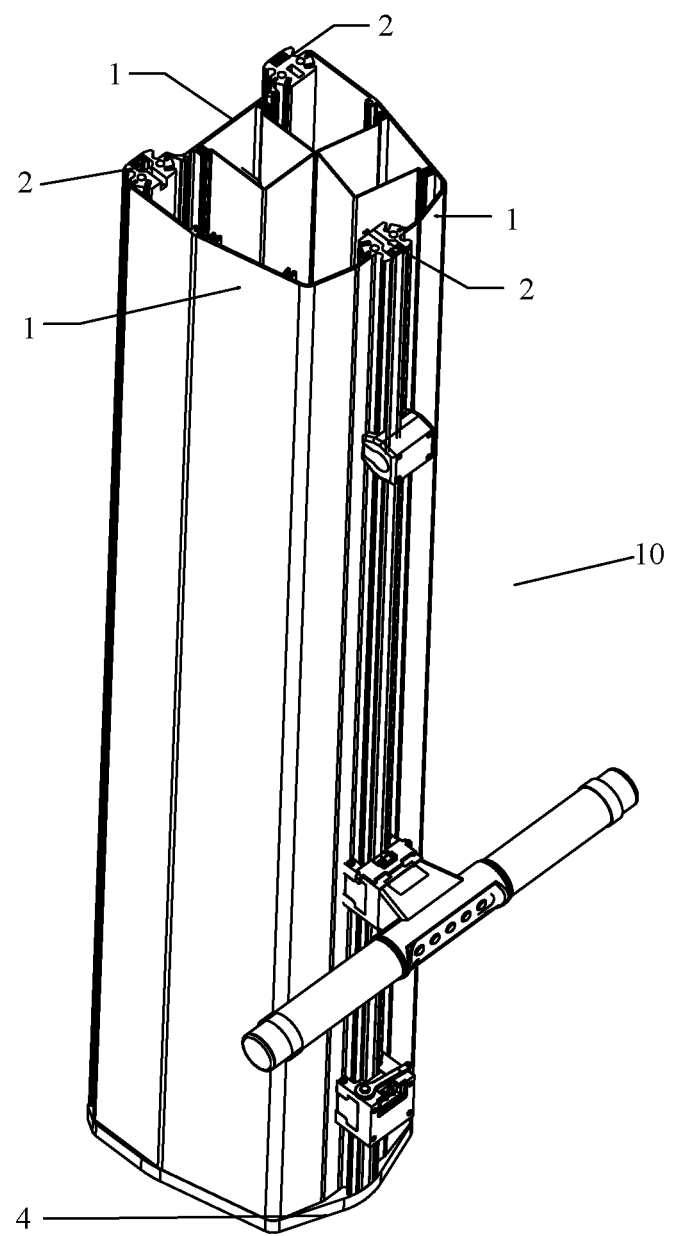
FIG. 2 is the three-dimensional view for the medical pendant box body of an exemplary embodiment of the present invention, in which the upper base plate is removed for clarity.
Figure 3:
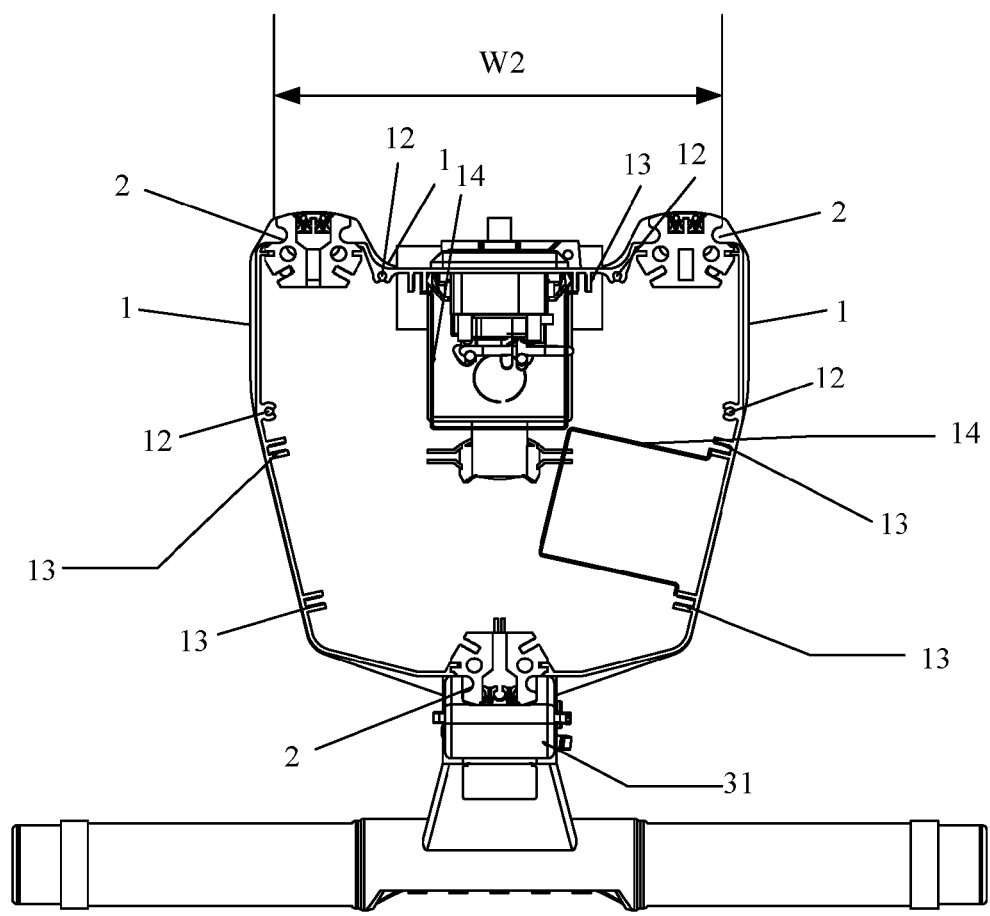
FIG. 3 is the top view of the medical pendant box body shown in FIG. 2.
Figure 4:
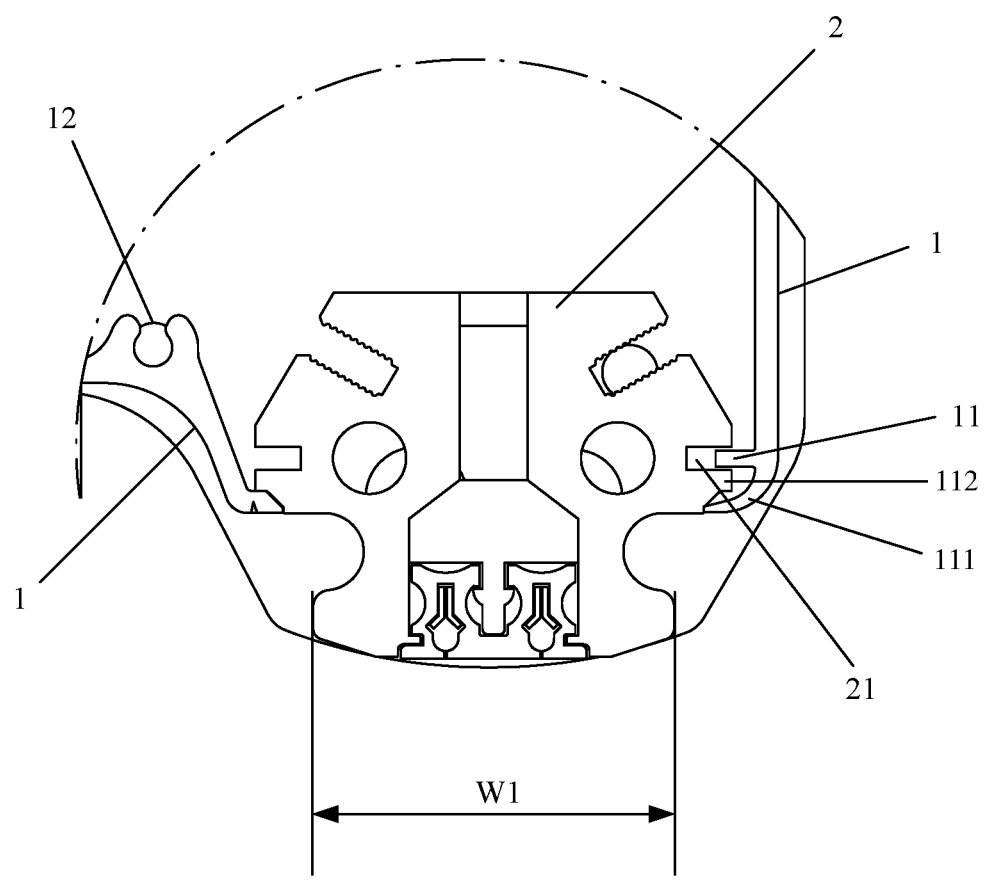
FIG. 4 is the partial enlarged view of a portion of the top left corner of FIG. 3, in which the portion of the top left corner of FIG. 3 is rotated by 180 degrees for clarity.

FIG. 1 and FIG. 2 respectively show the three-dimensional views for the medical pendant box body 10 of the first exemplary embodiment of the present disclosure, in which the upper base plate is removed from the medical pendant box body 10 in FIG. 2 for clarity. FIG. 3 shows the top view of the medical pendant box body 10 shown in FIG. 2. FIG. 4 shows the partial enlarged view of a portion of the top left corner of FIG. 3, in which the portion of the top left corner of FIG. 3 is rotated by 180 degrees for clarity.

The medical pendant box body 10 of the present disclosure may comprise at least two panels 1, at least two posts 2 extending along the longitudinal direction of the medical pendant box body, an upper base plate 3 and a lower base plate 4, and at least two panels 1 being attached (e.g., fixed) to the at least two posts 2, respectively. The upper base plate 3 and the lower base plate 4 may be attached (e.g., fixed) to the upper edge and the lower edge of each panel 1 of at least two panels 1, respectively, a snap-fit portion 11 may be disposed (e.g., provided) at a side edge portion (e.g., on or near to at least one side edge) of one or more panels 1 of at least two panels 1, and a slot 21 may be provided on at least one side of each post 2 of at least two posts 2 configured to receive (e.g., for receiving) the corresponding snap-fit portion 11 of the corresponding panel 1. A portion 111 of the corresponding panel 1 may extend for example from snap-fit portion 11. Portion 111 may be an extension portion that is curved in shape (e.g., a curved portion), extending from snap-fit portion 11. Snap-fit portion 11 may be disposed at a first side of a protrusion 112 of post 2 and portion 111 may be disposed at a second side of protrusion 112 of post 2, so that snap-fit portion 11 and portion 111 substantially surround protrusion 112 (e.g., snap-fit portion 11 and portion 111 may fit around or fit around both sides of protrusion 112). Accordingly for example, protrusion 112 may be received within a recess formed by snap-fit portion 11 and portion 111. Protrusion 112 may be disposed at a side of slot 21 and may help to form slot 21 (e.g., partially form slot 21) of post 2.

In this way, the medical pendant box body of the present disclosure can be installed using a small amount of screws or even not using a screw to achieve the suitable connection of the panels and posts as well as the (e.g., entire) box body, substantially without exposed screws on the surface of the panels, without using the silica gel or rubber sealing strips to mask the screws, which may facilitate the cleaning and disinfection. At least some exemplary embodiments may be capable of realizing the rapid disassembly and assembly of the medical pendant box body in a relatively short time.

Note that, "upper", "lower", "front", "rear", "left", "right" and the like used herein are only exemplary directions defined to facilitate the description of the exemplary embodiments, as shown in FIG. 3, the direction toward the reader is "upper", the direction away from the reader is "lower", the direction of the bottom side in the paper is "front", the direction of the top side in the paper is "rear", the direction of the left side in the paper is "left", and the direction of the right side in the paper is "right". Of course, those skilled in the art on the basis of the exemplary embodiments can understood that "upper", "lower", "front", "rear", "left", "right" and other directions can also be defined in other ways, which also fall into the protective scope of the present disclosure.

In at least some exemplary embodiments, the upper base plate 3 and the lower base plate 4 may each comprise a through-hole at or the in the vicinity of its periphery for a base plate-fixing screw to pass through, and a base plate-fixing threaded hole 12 may be provided at or in the vicinity of the upper edge and lower edge of each panel 1 of at least two panels 1 for receiving the corresponding base plate-fixing screw.

At least some of the exemplary embodiments provided above describe the case of the additional fixation of the base plates and the panels through the base plate-fixing screws. Also, for example, other fixing modes (for example, riveting, welding, etc.) can also be employed as long as the base plates can be fixed to the panels. Such variation is also contemplated in the present disclosure.

In this way, even though the base plates and the panels may be fixed via the base plate-fixing screws, the number of the screws (for example, in the embodiment shown in FIG. 3, use for example at upper and lower portions eight screws)

used in the medical pendant box body of the present disclosure has been also been significantly reduced as compared with the number of the screws (generally use several dozens) used in conventional medical pendant box bodies. Furthermore, there may be no exposed screws on the surface of the panels (for example, in the embodiment shown in FIG. 3, the screws may be located at the upper base plate and the lower base plate), without using the silica gel or rubber sealing strips to mask the screws. Such a configuration may facilitate cleaning and disinfection, being capable of realizing the rapid disassembly and assembly of the medical pendant box body in a relatively short time.

In at least some exemplary embodiments, for example as shown in FIGS. 1-4, the medical pendant box body 10 may comprise three panels 1 and three posts 2, the three panels 1 comprising two side panels with generally L-shaped cross sections and one rear panel with a generally I-shaped cross section.

In at least some exemplary embodiments, for example as shown in FIGS. 1-4, the cross section of the medical pendant box body 10 may be generally square or trapezoidal.

As shown in FIGS. 3 and 4, the medical pendant box body of at least some exemplary embodiments can be adapted for the mechanical connecting piece 31 with width W1 or W2. For example, a single post can be adapted for a mechanical connecting piece with a width of W1, and the interval between two posts can be adapted for a mechanical connecting piece with a width of W2. In at least some exemplary embodiments, W2>W1. The mechanical connecting piece can be used for installing various medical accessories, for example, a control handle, an infusion pole, a display arm, a medical guide rail, etc.

Figure 5:
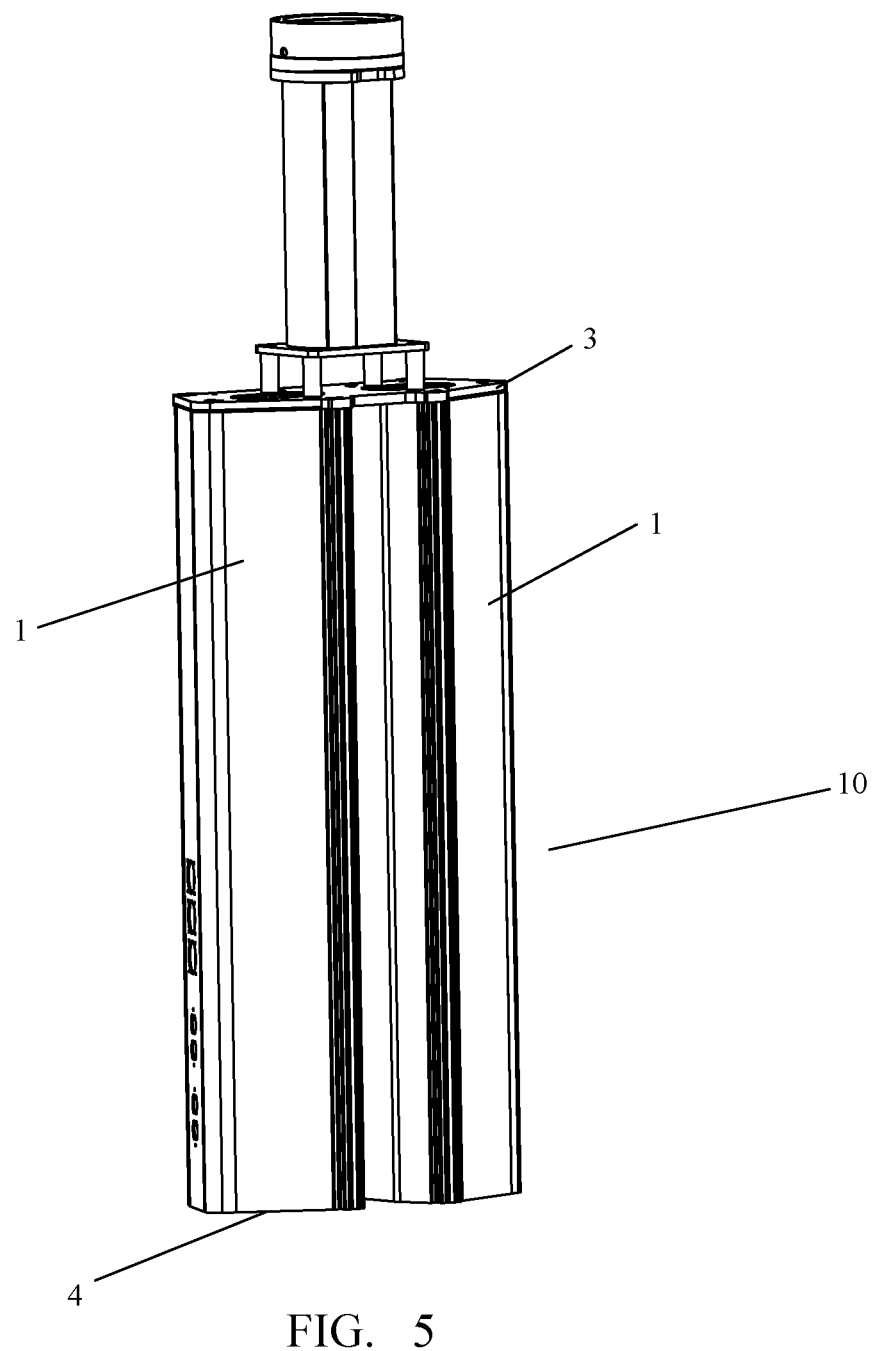
FIG. 5 is the three-dimensional view for the medical pendant box body of an exemplary embodiment of the present disclosure.
Figure 6:
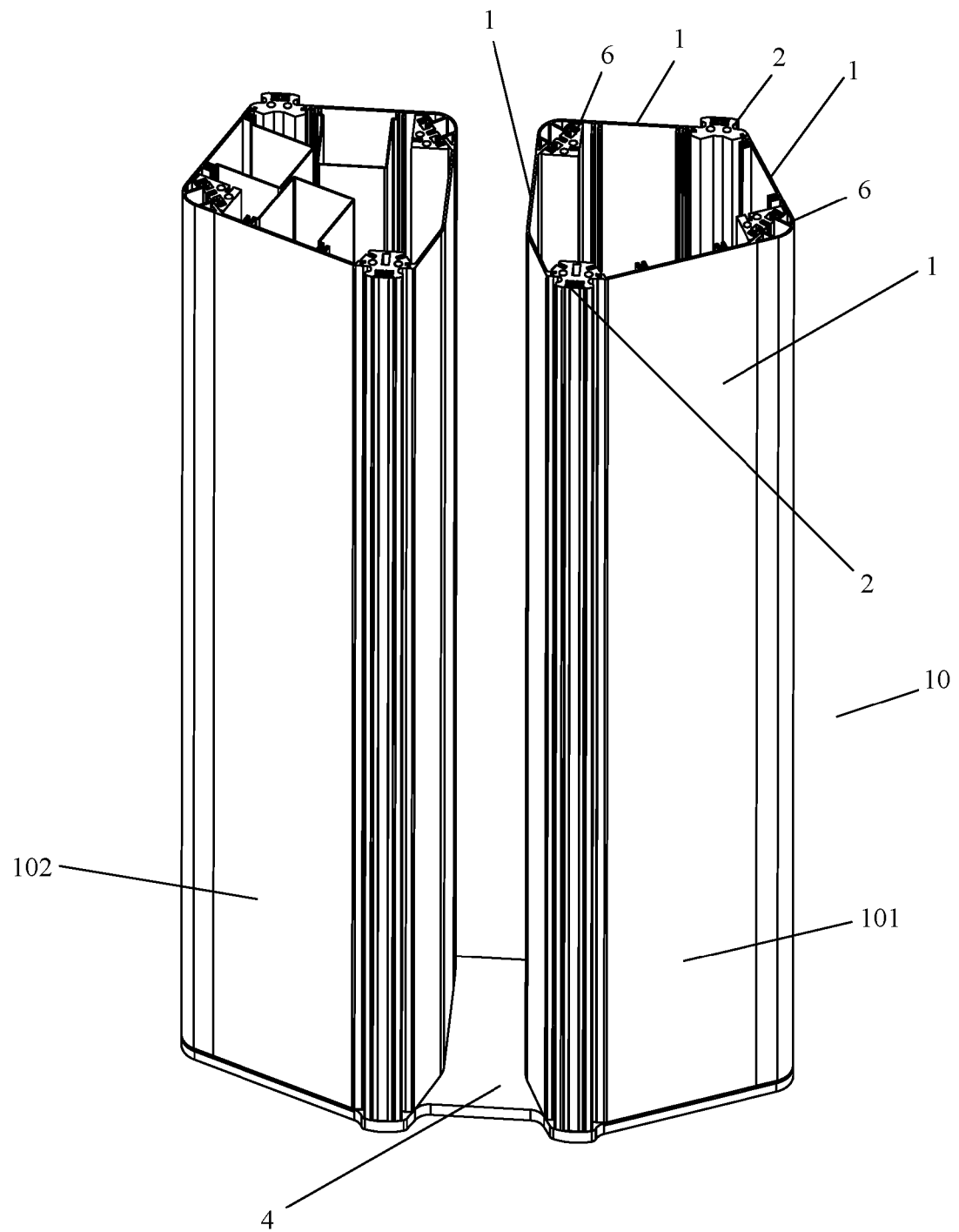
FIG. 6 is the three-dimensional view for the medical pendant box body of an exemplary embodiment, in which the upper base plate is removed for clarity.
Figure 7:
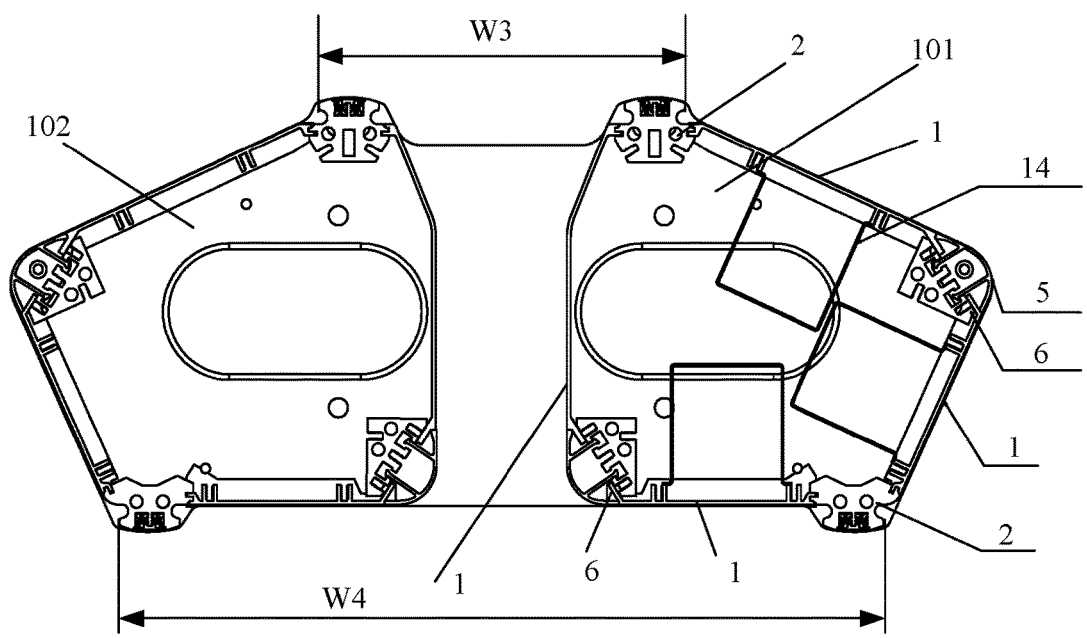
FIG. 7 is the top view of the medical pendant box body shown in FIG. 6, in which the anterior-posterior direction is turned by 180 degrees for clarity.
Figure 8:
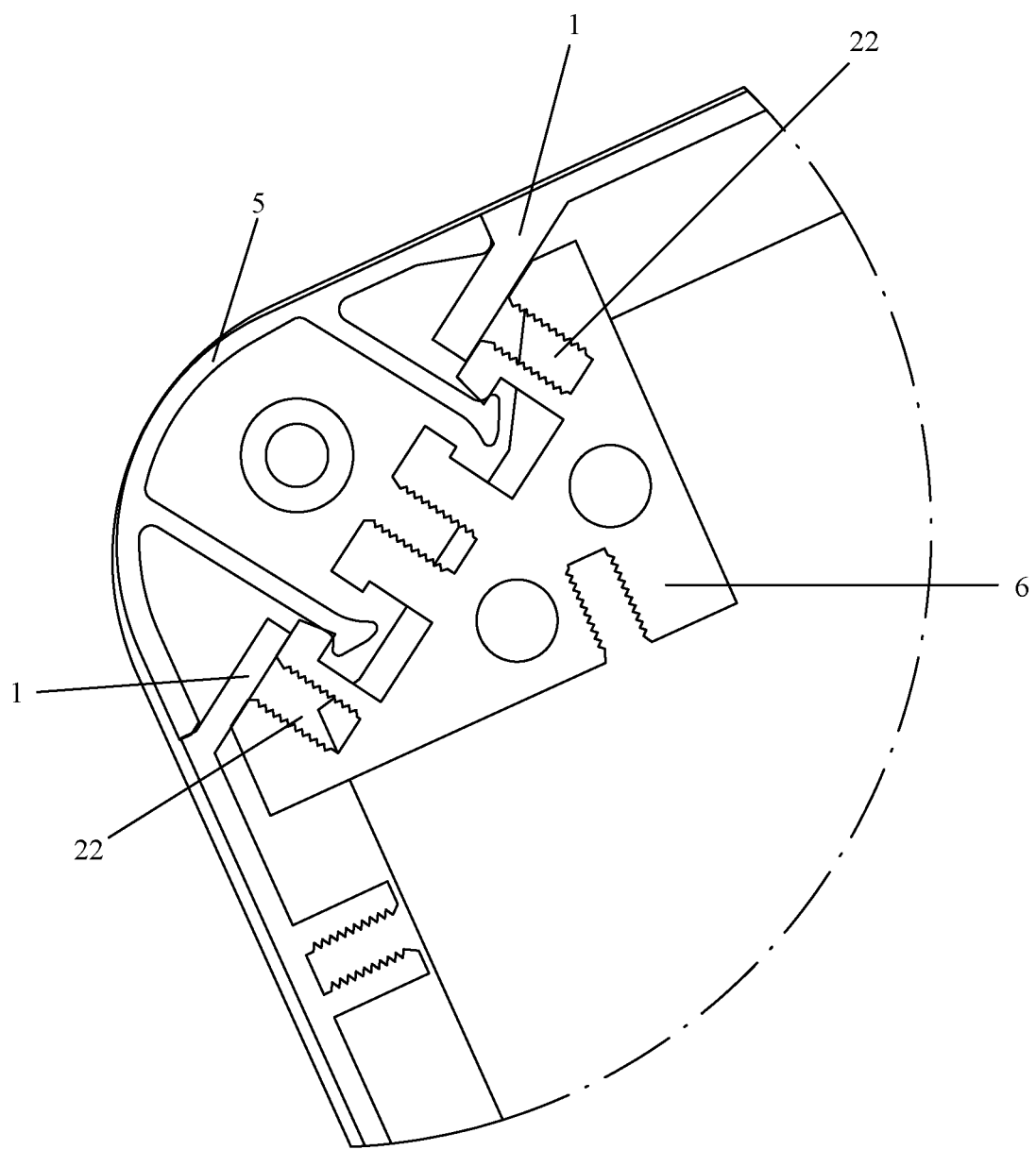
FIG. 8 is the partial enlarged view of a portion of the top left corner of FIG. 7.

FIG. 5 and FIG. 6 respectively show the three-dimensional views for the medical pendant box body 10 of another exemplary embodiment, in which the upper base plate is removed from the medical pendant box body 10 in FIG. 6 for clarity. FIG. 7 shows the top view of the medical pendant box body 10 shown in FIG. 6, in which the anterior-posterior direction is turned by 180 degrees for clarity. FIG. 8 shows the partial enlarged view of a portion of the top left corner of FIG. 7.

In at least some exemplary embodiments, for example as shown in FIGS. 5-8, the medical pendant box body 10 may comprise eight panels 1, four posts 2 and four auxiliary columns 6 extending along the longitudinal direction of the medical pendant box body. The eight panels 1 may comprise two side panels having generally L-shaped cross sections and six panels having generally I-shaped cross sections, in which the medical pendant box body 10 may comprise two sub-box bodies 101 and 102. Each sub-box body may comprise one side panel having a generally L-shaped cross section, three panels having generally I-shaped cross sections, two posts 2 and two auxiliary columns 6 (for example, in FIGS. 6 and 7, only the panels, posts, and auxiliary columns of the box body 101 are marked for clarity, but it should be understood that the constitution of the sub-box body 102 can be, for example, similar to the constitution of the sub-box body 101).

In at least some exemplary embodiments, for example as shown in FIGS. 5-8, an overall (e.g., total) cross section of the medical pendant box body 10 may be generally rectangular or trapezoidal, and the cross section of each sub-box body may be generally square or trapezoidal.

In at least some exemplary embodiments, for example as shown in FIGS. 5-8, there may be an interval between the two sub-box bodies, which may form a hollow area from top to bottom. In this way, the hollow area can be used as the cable management area of the medical pendant.

In at least some exemplary embodiments, the medical pendant box body can provide a larger space of box body and can be adapted for a mechanical connecting piece with wider width. In at least some exemplary embodiments, for example as shown in FIG. 7, a medical pendant box body can be adapted for the mechanical connecting pieces with widths W3 and W4. For example, the interval between the front two posts can be adapted for a mechanical connecting piece with a width of W3, and the interval between the rear two posts can be adapted for a mechanical connecting piece with a width of W4. In at least some exemplary embodiments, W4>W3.

In at least some exemplary embodiments, W3 can be made equal to W2 in order to make a mechanical connecting piece of the same width can be used for multiple exemplary embodiments of the medical pendant box body.

In at least some exemplary embodiments, the medical pendant box body may have a relatively larger box body space and relatively more panels and posts, for example to provide additional fixation. In at least some exemplary embodiments, for example as shown in FIGS. 5-8, auxiliary columns 6 may be provided with panel-fixing thread grooves 22 (for example as shown in FIG. 8) for receiving panel-fixing screws so as to for example attach (e.g., fix) at least one panel to the auxiliary columns. The medical pendant box body 10 may also comprise a side cover plate 5 for masking the panel-fixing screws.

In at least some exemplary embodiments (e.g., as shown in FIG. 7), two side panels with generally L-shaped cross sections may be removed, and two panels respectively located at the front side and the rear side and having generally I-shaped cross sections may be added.

In at least some exemplary embodiments, the medical pendant box body 10 may comprise eight panels 1, four posts 2 and four auxiliary columns 6, the eight panels 1 including eight panels having generally I-shaped cross sections.

In at least some exemplary embodiments, the cross section of the medical pendant box body 10 may be generally rectangular or trapezoidal.

The present disclosure is not limited to the particular number of panels and posts or the exemplary medical pendant box bodies above having a particular exemplary cross section shape, and other number of panels and posts and the medical pendant box bodies having other cross section shapes can also be provided.

For example, the medical pendant box body can comprise two panels and two posts, both the panels being generally in a shape which looks like the character "几" (e.g., Chinese character "ji"), so that the cross section shape of the medical pendant box body may be generally square; or both the panels having a generally semi-circular shape, for example so that the cross section shape of the medical pendant box body may be generally circular.

For example, the medical pendant box body can comprise four panels and four posts, all of the four panels may be generally I-shaped, so that the cross section shape of the medical pendant box body is generally square; or all of the four panels may be generally of a quarter of a circular shape, so that the cross section shape of the medical pendant box body is generally circular.

For example, the medical pendant box body can comprise five panels and five posts, all of the five panels being generally I-shaped, so that the cross section shape of the medical pendant box body may be generally pentagonal.

In view of the numerous exemplary variations, other number of panels and posts, and exemplary medical pendant box bodies having other cross section shapes are contemplated as well.

In at least some exemplary embodiments, auxiliary columns can be set according to predetermined design or no auxiliary column may be set, and if auxiliary columns are set, the setting modes of auxiliary columns are not limited to the embodiments give above, and other setting modes can be employed. For example, in addition to the panels, the posts, the upper base plate and the lower base plate, the medical pendant box body 10 can also comprise auxiliary columns 6 extending along the longitudinal direction of the medical pendant box body, the auxiliary columns 6 being provided with panel-fixing thread grooves 22 for receiving the panel-fixing screws so as to fix at least one panel 1 to auxiliary columns 6.

Figure 9:
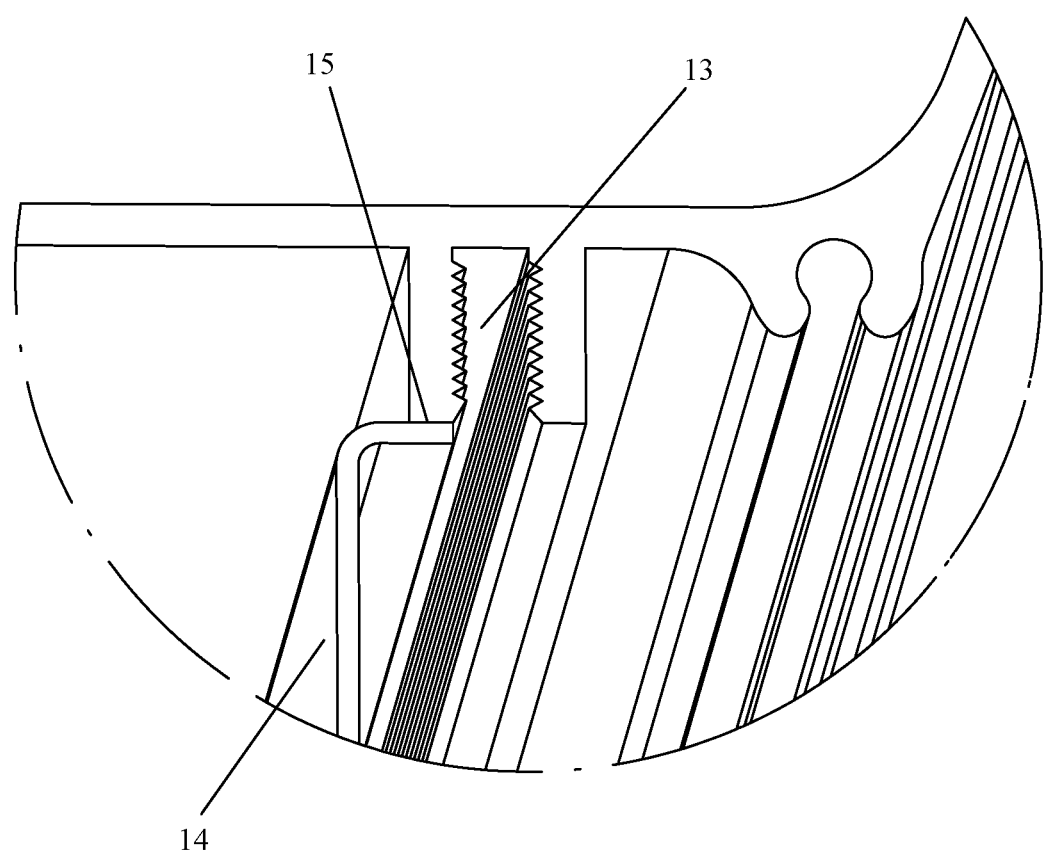
FIG. 9 is the partial enlarged view showing the details of the spare thread grooves and separator in the medical pendant box body.

As shown in FIGS. 3 and 9, for example, at least two spare thread grooves 13 may be provided on the internal surface of panels 1. For example, these spare thread grooves 13 can extend along the longitudinal direction of the medical pendant box body and may pass through the entire length of the medical pendant box body.

For example, a spacing (e.g., the distances) among the at least two spare thread grooves 13 on each panel 1 may be substantially equal. For example, as shown in FIG. 3, the distance between the two spare thread grooves 13 on the left panel may be substantially equal to the distance between the two spare thread grooves 13 on the right panel.

For example, the medical pendant box body 10 may also comprise a separator 14, the edge part of the separator 14 pressing against the top surface 15 of the periphery of the groove of the spare thread grooves 13 via the head of the separator-fixing screw.

For example, separator 14 may be an electrical separator so as to provide electrical isolation among the various internal components in the medical pendant box body 10.

For example, the cross section of the separator 14 may be generally in a shape which looks like the character "几" (Chinese character "ji").

For example, as shown in FIGS. 2 and 6, posts 2 may extend along the longitudinal direction of the medical pendant box body 10 and may pass through the (e.g., entire) length of the medical pendant box body 10. In this way, via a mechanical connecting piece, the location of the medical accessories can be steplessly adjusted along the longitudinal direction of the medical pendant box body.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:

1. A medical pendant box body, comprising:
   a first panel and a second panel;
   a first post and a second post extending along a longitudinal direction of the medical pendant box body; and
   an upper base plate and a lower base plate;
   wherein the first panel is attached to the first post and the second panel is attached to the second post;
   wherein the upper base plate is attached to an upper edge of each of the first and second panels, and the lower base plate is attached to a lower edge of each of the first and second panels;
   wherein a snap-fit portion is disposed at a side edge portion of at least one of the first panel and the second panel;
   wherein a slot configured to receive the snap-fit portion is provided at at least one side of at least one of the first post and the second post;
   wherein a protrusion is disposed at a side of the slot;
   wherein an extension portion extends from the snap-fit portion; and
   wherein the protrusion is received within a recess formed by the snap-fit portion and the extension portion.

2. The medical pendant box body of claim 1, wherein the upper base plate and the lower base plate each include:
   a through-hole disposed at or in the vicinity of a periphery of each of the upper base plate and the lower base plate, each through-hole configured to receive a base plate-fixing screw; and
   a base plate-fixing threaded hole configured to receive the corresponding base plate-fixing screw is provided in each of the first and second panels or in the vicinity of the upper edge and lower edge of each of the first and second panels.

3. The medical pendant box body of claim 1, further comprising a third panel that is attached to a third post.

4. The medical pendant box body of claim 1, wherein the cross section of the medical pendant box body is generally square or trapezoidal.

5. The medical pendant box body of claim 1, further comprising:
   a third panel, a fourth panel, a fifth panel, a sixth panel, a seventh panel, and an eighth panel, each of the panels having two side panels each having a generally L-shaped cross section;
   a third post and a fourth post; and
   a first auxiliary column, a second auxiliary column, a third auxiliary column, and a fourth auxiliary column, each of the auxiliary columns extending along the longitudinal direction of the medical pendant box body;
   wherein the medical pendant box body is divided into a first sub-box body and a second sub-box body;
   the first sub-box body including:
      the first, second, third, and fourth panels, wherein one of the first, second, third, and fourth panels has a generally L-shaped cross section and three of the first, second, third, and fourth panels have a generally I-shaped cross section,
      the first post and the second post, and
      the first auxiliary column and the second auxiliary column; and
   the second sub-box body including:
      the fifth, sixth, seventh, and eighth panels, wherein one of the fifth, sixth, seventh, and eighth panels has a generally L-shaped cross section and three of the fifth, sixth, seventh, and eighth panels have a generally I-shaped cross section,
      the third post and the fourth post, and
      the third auxiliary column and the fourth auxiliary column.

6. The medical pendant box body of claim 5, wherein an overall cross section of the medical pendant box body is generally rectangular or trapezoidal, and the cross section of each of the first and second sub-box bodies is generally square or trapezoidal.

7. The medical pendant box body of claim 5, wherein there is an interval between the first and second sub-box bodies that forms a hollow area from top to bottom.

8. The medical pendant box body of claim 5, wherein at least one of the first, second, third, and fourth auxiliary columns are provided with a panel-fixing thread groove configured to receive a panel-fixing screw so as to attach at least one panel to at least one auxiliary column.

9. The medical pendant box body of claim 8, further comprising a side cover plate that masks the panel-fixing screw.

10. A medical pendant box body, comprising:
a first panel and a second panel;
a first post and a second post extending along a longitudinal direction of the medical pendant box body; and
an upper base plate and a lower base plate;
wherein the first panel is attached to the first post and the second panel is attached to the second post;
wherein the upper base plate is attached to an upper edge of each of the first and second panels, and the lower base plate is attached to a lower edge of each of the first and second panels;
wherein a first snap-fit portion is disposed at a side edge portion of the first panel, and a second snap-fit portion is disposed at a side edge portion of the second panel;
wherein a first slot configured to receive the first snap-fit portion is provided at a side of the first post, and a second slot configured to receive the second snap-fit portion is provided at a side of the second post; and
wherein at least two spare thread grooves are provided at an internal surface of each of the first panel and the second panel.

11. The medical pendant box body of claim 10, wherein spacing between the at least two spare thread grooves on each of the first and second panels is equal.

12. The medical pendant box body of claim 10, further comprising a separator, an edge part of the separator pressing against a top surface of a periphery of a groove of the at least two spare thread grooves via a head of a separator-fixing screw.

13. The medical pendant box body of claim 12, wherein a cross section of the separator has a general shape of a character "几".

14. The medical pendant box body of claim 10, further comprising a plurality of auxiliary columns extending along the longitudinal direction of the medical pendant box body, the plurality of auxiliary columns having panel-fixing thread grooves configured to receive panel-fixing screws so as to attach at least one of the first and second panels to the at least one of the plurality of auxiliary columns.

15. A medical pendant box body, comprising:
a first panel and a second panel;
a first post and a second post extending along a longitudinal direction of the medical pendant box body; and
an upper base plate and a lower base plate;
wherein the first panel is attached to the first post and the second panel is attached to the second post;
wherein the upper base plate is attached to an upper edge of each of the first and second panels, and the lower base plate is attached to a lower edge of each of the first and second panels;
wherein a snap-fit portion is disposed at a side edge portion of at least one of the first panel and the second panel;
wherein a slot configured to receive the snap-fit portion is provided at at least one side of at least one of the first post and the second post;
wherein an extension portion extends from the snap-fit portion;
wherein a protrusion is disposed at a side of the slot; and
wherein the snap-fit portion and the extension portion fit around both sides of the protrusion.

16. The medical pendant box body of claim 15, wherein the protrusion is disposed at the side of the slot to partially form the slot.

17. The medical pendant box body of claim 15, wherein the snap-fit portion and the extension portion substantially surround the protrusion.

18. The medical pendant box body of claim 15, wherein the protrusion is received within a recess formed by the snap-fit portion and the extension portion.

19. The medical pendant box body of claim 15, wherein the extension portion is curved in shape.

\* \* \* \* \*